US009005528B2

(12) United States Patent  (10) Patent No.: US 9,005,528 B2
Coleman et al.  (45) Date of Patent: Apr. 14, 2015

(54) SAMPLING CONTAINER FOR COLLECTION OF FLUIDS

(75) Inventors: Todd Coleman, Fairmount, IL (US); Corben Rice, Penfield, IL (US); Dennis Coleman, Champaign, IL (US)

(73) Assignee: Weatherford Switzerland Trading and Development GmbH, Zug (CH)

( * ) Notice: Subject to any disclaimer, the term of this patent is extended or adjusted under 35 U.S.C. 154(b) by 432 days.

(21) Appl. No.: 13/419,925

(22) Filed: Mar. 14, 2012

(65) Prior Publication Data
US 2012/0234114 A1  Sep. 20, 2012

Related U.S. Application Data

(60) Provisional application No. 61/465,086, filed on Mar. 14, 2011.

(51) Int. Cl.
*G01N 1/22* (2006.01)
*G01N 1/40* (2006.01)
*G01N 31/22* (2006.01)
*G01N 33/00* (2006.01)

(52) U.S. Cl.
CPC .............. *G01N 1/22* (2013.01); *G01N 1/4044* (2013.01); *G01N 31/224* (2013.01); *G01N 33/0044* (2013.01)

(58) Field of Classification Search
CPC ..... G01N 1/22; G01N 1/2247; G01N 1/4044; G01N 31/224; G01N 33/0013; G01N 33/0044
USPC ............................ 73/863.71; 422/86; 436/121
See application file for complete search history.

(56) References Cited

U.S. PATENT DOCUMENTS 3,353,411 A  11/1967 Nadeau et al.
3,374,678 A   3/1968 McGuckin
(Continued)

FOREIGN PATENT DOCUMENTS

DE  3131698 A1 * 3/1983 ............. G01N 31/22
DE  4021556 A1 * 1/1992 ............. G01N 31/22
(Continued)

OTHER PUBLICATIONS

PCT Search Report and Written Opinion for International Application No. PCT/US2012/028995 dated Jun. 26, 2012.
(Continued)

*Primary Examiner* — Thomas P Noland
(74) *Attorney, Agent, or Firm* — Patterson & Sheridan, L.L.P.

(57) ABSTRACT

A method and apparatus for the collection, transportation and analysis of gas samples which may be required in various scientific, environmental and natural resource contexts is provided. The apparatus comprises a sampling container assembly for sampling a fluid. The container assembly comprises a body defining a sampling chamber having a first end and a second end, a first valve assembly fluidly coupled with the first end and a reactant material positioned within the sampling chamber for reacting with the fluid. After collection of the sample in the sampling container assembly, hazardous fluids are converted to non-hazardous materials that can be transported without additional hazardous material restraints. Further, the flow through design of the sampling container assembly allows for the collection of gases such as $H_2S$ at low concentrations by flowing the gas over the reactant materials for longer periods of time.

27 Claims, 3 Drawing Sheets

(56) References Cited

U.S. PATENT DOCUMENTS

| | | | |
|---|---|---|---|
| 3,545,930 A | * | 12/1970 | Czenkusch et al. ..... G01N 31/22 |
| 4,800,067 A | * | 1/1989 | Heckmann et al. ............. 422/86 |
| 4,919,955 A | | 4/1990 | Mitchell |
| 4,951,496 A | | 8/1990 | Aarts |
| 5,047,073 A | | 9/1991 | Stetter et al. |
| 5,171,535 A | * | 12/1992 | Lamont .................... G01N 1/22 |
| 5,834,626 A | * | 11/1998 | De Castro et al. .......... 422/86 X |
| 6,948,391 B2 | | 9/2005 | Brassell et al. |
| 7,647,846 B2 | | 1/2010 | Coleman et al. |
| 7,757,572 B2 | | 7/2010 | Coleman et al. |
| 2001/0012635 A1 | * | 8/2001 | Ibaraki et al. ........ G01N 31/224 |
| 2004/0014489 A1 | | 1/2004 | Miyachi et al. |
| 2008/0076185 A1 | * | 3/2008 | Bohm et al. ......... G01N 31/224 |
| 2008/0282814 A1 | | 11/2008 | Coleman et al. |
| 2009/0084720 A1 | | 4/2009 | Dannenmaier et al. |
| 2009/0260416 A1 | | 10/2009 | Coleman et al. |

FOREIGN PATENT DOCUMENTS

| | | | | |
|---|---|---|---|---|
| EP | 225520 A2 | * | 6/1987 | ............... G01N 1/22 |
| GB | 1438913 A | * | 6/1976 | ............ G01N 31/22 |
| GB | 2 253 905 | | 9/1992 | |
| GB | 2473317 A | * | 3/2011 | ............ G01N 31/22 |
| WO | WO 2007/140406 A2 | | 12/2007 | |
| WO | WO 2007/140406 A3 | | 12/2007 | |

OTHER PUBLICATIONS

Jean P. Pare, A New Tape Reagent for the Determination of Hydrogen Sulfide in Air, Journal of the Air Pollution Control Association, Jun. 1966, pp. 325-327, vol. 16, No. 6.

* cited by examiner

SAMPLING CONTAINER FOR COLLECTION OF FLUIDS

CROSS-REFERENCE TO RELATED APPLICATIONS

This application claims benefit of U.S. Provisional Patent Application Ser. No. 61/465,086, filed Mar. 14, 2011, which is herein incorporated by reference in its entirety.

BACKGROUND OF THE INVENTION

1. Field of the Invention

Embodiments of the present invention generally relate to containers and methods for the collection, transportation and analysis of fluid samples which may be required in various scientific, environmental and natural resource contexts.

2. Description of the Related Art

Having the ability to collect, differentiate and categorize different gas mixtures and their individual components has long been a necessity for the purposes of energy exploration and source identification of stray gases (i.e., differentiating gases from landfills, gas storage fields, producing wells, etc.). However, in order to do so successfully, one often needs to obtain samples from different potential source gases, and then submit the samples for detailed testing and comparison. Because analysis of the chemical composition can often be inconclusive in differentiating similar gases, isotope analysis of individual components of the gas can often provide an effective means of distinguishing two otherwise chemically identical gas sources. For instance, methane from a sanitary landfill is isotopically different from methane associated with petroleum. Similarly, isotope analysis of certain gas components can also provide insight to the mechanism of formation of the gases, and therefore give insight into the commercial viability of the gas source. Unfortunately, the transfer and shipment of hazardous materials (e.g., flammable and/or toxic gases) is often costly and usually requires specialized training. In some instances, air shipment of such gases is strictly forbidden (i.e. toxic gases). One such component of interest often associated with natural gas is hydrogen sulfide ($H_2S$).

Typical ways of collecting gases containing hydrogen sulfide ($H_2S$) have included the use of containers like gas bags, chemically treated metal cylinders, and glass vials. Such containers are often fragile, expensive and unwieldy. In some instances, samples containing toxic concentrations of $H_2S$ are strictly forbidden on aircraft. In parts of the world where isotope analysis is not available, the only means of transporting such samples to a laboratory with isotope analysis capability would be via ocean freight, and then via ground transport. This procedure often consumes valuable time and resources, as the shipping of hazardous materials involves specialized training for the shipper as well as associated hazardous shipping fees and restrictions. $H_2S$ is also highly reactive and may react with the vessel in which it is contained. For instance, untreated stainless steel cylinders can completely "remove" $H_2S$ from a gas mixture.

Once in the lab, the current technology for extracting sulfur from $H_2S$ for isotopic analysis is to flow the gas through various solutions. The current solutions include cadmium acetate, silver phosphate, zinc acetate, and silver phosphate/silver nitrate solutions. All of these methods utilize liquid solutions and except for zinc acetate are hazardous.

Therefore, there is a need for containers and methods for the collection, transportation, and analysis of fluid samples with reduced costs.

SUMMARY OF THE INVENTION

Embodiments of the present invention generally relate to containers and methods for the collection, transportation and analysis of fluid samples which may be required in various scientific, environmental and natural resource contexts. In one embodiment a container assembly for sampling a fluid is provided. The container assembly includes a body defining a sampling chamber having a first end and a second end, a first valve assembly fluidly coupled with the first end and a reactant material positioned within the sampling chamber for reacting with the fluid.

In another embodiment a container assembly for sampling a fluid includes a body defining a sampling chamber having a first end and a second end, a first valve assembly fluidly coupled with the first end, a second valve assembly fluidly coupled with the second end, an indicator material positioned within the chamber for identifying the presence of a fluid, a reactant material positioned within the chamber for reacting with the fluid, and a filtering material positioned within the chamber for controlling flow and separating the indicator material from the reactant material.

In yet another embodiment, a method for sampling a hydrogen sulfide gas is provided. The method comprises flowing a gas containing hydrogen sulfide into a sampling container assembly, wherein the container assembly includes a reactant material, reacting the hydrogen sulfide with the reactant material, and converting the hydrogen sulfide to an inert form.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments of the present invention provide sample containers and methods for the safe and cost efficient collection, transportation and analysis of fluid samples. In certain embodiments described herein, the containers and methods provided herein circumvent current hazardous materials regulations by chemically changing hazardous gases (e.g., $H_2S$) into a material that is non-hazardous and therefore can be shipped by traditional means (e.g., post, courier service, or air freight). Thus eliminating the need for HAZMAT training for the shipper as well as fees associated with the shipment of hazardous materials. Furthermore, the size of the containers described herein will also result in substantially reduced shipping costs for the user.

Figure 1:
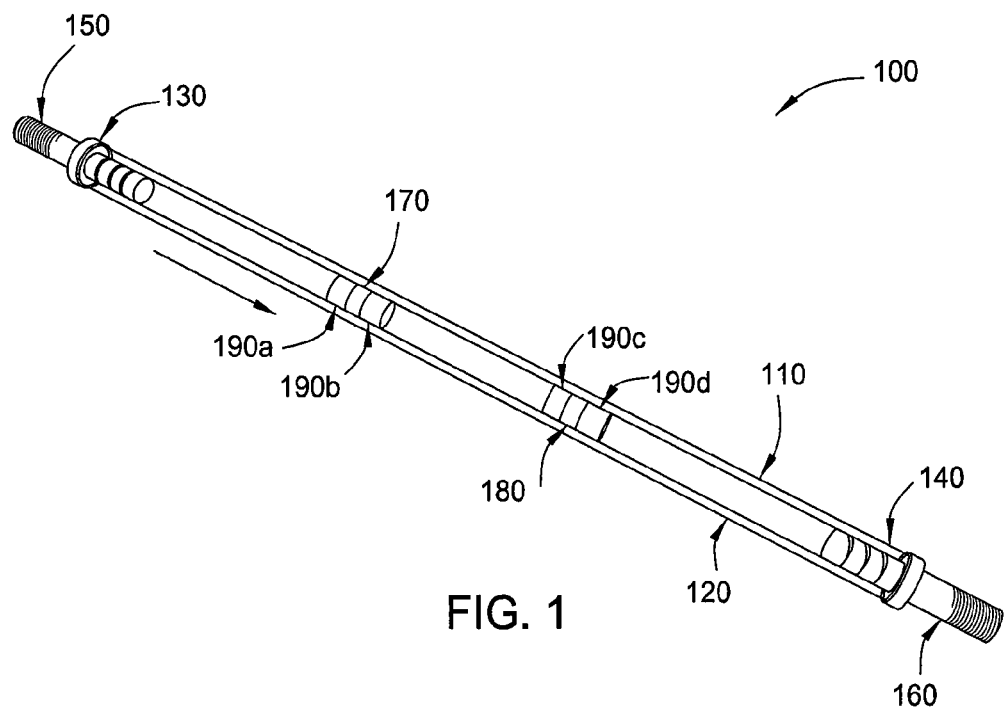
FIG. 1 is a perspective view of one embodiment of a sampling container assembly according to embodiments described herein.

FIG. 1 is a perspective view of one embodiment of a sampling container assembly 100. The sampling container assembly 100 includes a body 110 having a first end 130 and a second end 140. The body 110 defines a sampling chamber 120 for holding a compound. The compound may be a sampling fluid such as a gas. The gas may be a hazardous or non-hazardous material. The sampling fluid may enter the sampling chamber 120 and be partially converted to a different compound and/or phase containing the component for analysis while within the sampling chamber 120. For example, the sampling fluid may enter the sampling chamber 120 as a hazardous material and be converted to a non-hazardous or inert form while within the sampling chamber 120. Exemplary gases include hydrogen sulfide ($H_2S$) containing gases, carbon monoxide (CO) containing gases, carbon dioxide ($CO_2$) containing gases, and hydrocarbon containing gases.

The sampling container assembly 100 may be a flow through container assembly. The body 110 may be constructed of any material that does not substantially react with the fluid. Exemplary materials for constructing the body 110 include metal, aluminum, steel, plastic, polymer based material, carbon fiber or combinations thereof. The body 110 may comprise an opaque, transparent or semitransparent material. The body 110 may be any shape configured to hold the fluid. Exemplary shapes of the body 110 include a cylindrical or tubular body shape.

A first valve assembly 150 may be coupled to the first end 130 of the body and a second valve assembly 160 may be coupled to the second end 140 of the body. The first valve assembly 150 and the second valve assembly 160 may be self sealing for retaining the sampling fluid within the sampling chamber 120. The first valve assembly 150 and the second valve assembly 160 may be pneumatic valve assemblies. Exemplary valves assemblies include Schrader valves (typically comprising a valve stem into which a valve core is threaded—the valve core may be a poppet valve assisted by a spring), Presta valves and Dunlop valves. The first valve assembly 150 and the second valve assembly 160 may be coupled to the body 110 using any suitable attachment mechanism known in the art. Exemplary attachment mechanisms include hose barbs.

A reactant material 170 is positioned within the sampling chamber 120 for reacting with the sampling fluid. The reactant material 170 may comprise any material suitable for interacting with the sampling fluid and "trapping" the fluid via chemical or other suitable ways. The reactant material 170 may trap or convert the sampling fluid to a different compound and/or phase containing the component for analysis while within the sampling chamber. For example, the sampling fluid may be converted to an inert (and/or non-hazardous) form for subsequent shipment or analysis. Typically, the reactant material 170 is selected such that the reactant material 170 does not contain the component for isotopic analysis. For example, if the sampling fluid is $H_2S$ and the component for analysis is sulfur then the initial reactant material 170 would not contain sulfur. The reactant material may be in any form sufficient to allow the desired flow of fluid throughout the sampling chamber 120. The reactant material 170 may be a solid material such as a powder or granular material. The reactant material 170 may have any suitable size. For example, the reactant material 170 may have a grain size between about 0.1 mm and about 1 mm across. In another example, the reactant material 170 may have a grain size between about 0.3 mm and about 0.5 mm across. In certain embodiments the reactant material may be selected from zinc carbonate hydroxide ($Zn_5(CO_3)_2(OH)_6$), iron III oxide hydrate (2FeO(OH)), zinc acetate ($2(C_2H_3O_2)_2Zn$), iron oxide ($Fe_2O3$), and combinations thereof. The amount of reactant material 170 positioned within the sampling chamber 120 is sufficient to react with the fluid and convert the sampling fluid to a different compound and/or phase containing the component for analysis, for example, converting the sampling fluid to a non-hazardous or inert form, without substantially restricting the flow of fluid through the sampling chamber 120. In one example, the amount of reactant material 170 positioned within the sampling chamber 120 may be between 10 mg and 200 mg. In another example, the amount of reactant material 170 positioned within the sampling chamber 120 may be between 10 mg and 80 mg. In yet another embodiment, the amount of reactant material 170 positioned within the sampling chamber 120 may be between 40 mg and 50 mg.

An indicator material 180 may be positioned within the sampling chamber 120. The indicator material 180 may be used for indicating the presence or absence of the sampling fluid. The indicator material 180 may be used to indicate that the aforementioned reactant material 170 has been completely converted or saturated with the fluid. The indicator material 180 may undergo a visible change color to indicate the presence or absence of the sampling fluid. As depicted in FIG. 1, if present, the indicator material 180 may be positioned downstream from the reactant material and therefore will not begin to change color until all of the reactant material has sufficiently reacted with the fluid. The indicator material 180 may comprise any material capable of indicating the presence of the fluid. In certain embodiment, the indicator material 180 identifies the presence of $H_2S$ and indicates when the reaction of $H_2S$ with the reactant material is complete. The indicator material 180 may be selected from lead acetate, copper sulfate, and combinations thereof. The indicator material 180 may be a solid material such as a powder or granular material. The indicator material 180 may have any suitable size. In one example, the indicator material 180 may have a grain size between about 1 micron and about 50 microns across. In another example, the indicator material 180 may have a grain size between about 1 micron and about 20 microns across. In yet another example, the indicator material 180 may have a grain size between about 5 microns and about 10 microns across. The indicator material 180 may be present in an amount sufficient to allow multiple reads while allowing for efficient flow of the fluid through the sampling chamber 120. In one example, the amount of indicator material 180 positioned within the sampling chamber 120 may be between 50 grams and 400 grams. In another example, the amount of indicator material 180 positioned within the sampling chamber 120 may be between 100 grams and 200 grams. In yet another example, the amount of indicator material 180 positioned within the sampling chamber 120 may be between 130 grams and 150 grams.

Optionally, a filter material 190a-d may be positioned within the sampling chamber 120. The filter material 190a-d may be used for holding the reactant material 170 and indicator material 180 in place without substantially interfering with the flow-though properties of the sampling container assembly 100. The ability to keep the reactant material 170 and indicator material 180 compact and in place provides for uniform flow of the fluid over the reactant material 170 and the indicator material 180. The filter material 190a-d also controls the flow of fluid by diffusing the fluid through the reactant evenly, to avoid channeling of the fluid flow through only a small portion of the reactant which could result in an inadequate sample collection. The filter material 190a-d may be a material that is inert relative to the fluids in the sampling chamber 120. Exemplary filter materials 190a-d include polyethylene (PE) and polytetrafluoroethylene (PTFE) based materials. The filter material 190a-d may be an inert fibrous, porous, or sintered filtering material. The pores of the filter material 190a-d are typically smaller than the grain size of the either the reactant material 170 or the indicator material 180.

As depicted in FIG. 1, the filter material 190a and 190b are positioned on either side of the reactant material 170 to hold the reactant material 170 in place and the filter material 190c and 190d are positioned on either side of the indicator material 180 to hold the indicator material 180 in place. It should be understood that although four filters 190a-d are depicted in FIG. 1, any number of filters may be used in the sampling container assembly 100.

In operation, a sampling fluid enters the sampling chamber 120 via the first valve assembly 150. The sampling fluid may be a hazardous or non-hazardous fluid. The sampling fluid flows through the filter material 190a and contacts the reactant material 170, whereby the sampling fluid reacts with the reactant material 170. The reaction at least partially converts the sampling fluid to a different compound and/or phase containing the component for analysis. For example, the reaction with the reactant may convert at least some of the sampling fluid from fluid phase to a solid phase. Some of the sampling fluid flows through the filter material 190c and contacts the indicator material 180 to indicate the presence of the sampling fluid. In one example, when substantially all of the reactant material is saturated/reacted (i.e., the reactant material has been used up via reaction with the sampling fluid) any additional sampling fluid continues to flow through the used up reactant material toward the downstream indicator material 180. The additional sampling fluid flows through the filter material 190c and contacts the indicator material 180 thus indicating that substantially all of the reactant material has been used up and the desired amount of the product containing the component for analysis has been collected. The additional sampling fluid may flow through the filter material 190d and exit the sampling chamber 120 via the second valve assembly 160.

In one embodiment, a sampling fluid containing hazardous material enters the sampling chamber 120 via the first valve assembly 150. The sampling fluid flows through the filter material 190a and contacts the reactant material 170, whereby the hazardous material reacts with the reactant material 170. The reaction at least partially converts the hazardous material to a non-hazardous compound and/or different phase containing the component for analysis. For example, the reaction with the reactant may convert at least some of the hazardous material from fluid phase to a non-hazardous solid phase. Some of the sampling fluid flows through the filter material 190c and contacts the indicator material 180 to indicate the presence of the hazardous sampling fluid. In one example, when substantially all of the reactant material is saturated/reacted (i.e., the reactant material has been used up via reaction with the hazardous fluid) any additional hazardous sampling fluid continues to flow through the used up reactant material toward the downstream indicator material 180. The additional hazardous fluid flows through the filter material 190c and contacts the indicator material 180 thus indicating that substantially all of the reactant material has been used up and the desired amount of the non-hazardous product containing the component for analysis has been collected. The additional hazardous fluid may flow through the filter material 190d and exit the sampling chamber 120 via the second valve assembly 160.

Figure 2:
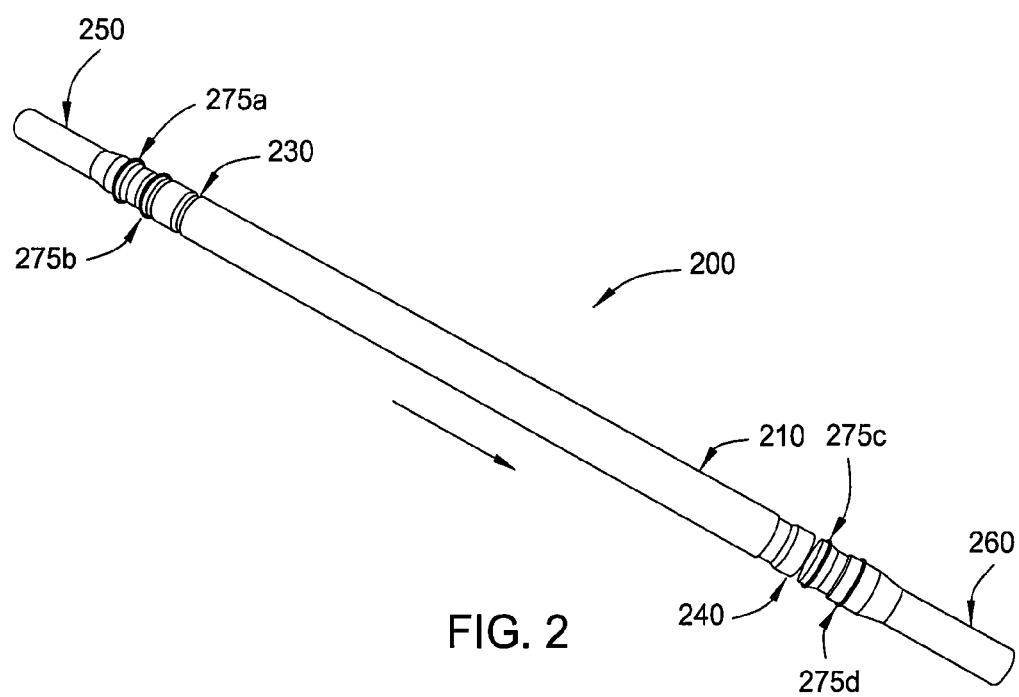
FIG. 2 is a perspective view of another embodiment of a sampling container assembly according to embodiments described herein.

FIG. 2 is a perspective schematic view of another embodiment of a sampling container assembly 200 according to embodiments described herein. The sampling container assembly 200 is similar to the sampling container assembly 100 depicted in FIG. 1 except that the body 210 includes an opaque material and swaging is used to hold a first valve assembly 250 and a second valve assembly 260 in place. The sampling container assembly 200 is suitable for sampling in situations where a visible indicator material (e.g., color changing material) is not needed. The body 210 has a first end 230 and a second end 240 and defines a sampling chamber (not visible) similar to sampling chamber 120 for holding a fluid. The sampling chamber contains a reactant material (not visible) similar to reactant material 170. The sampling chamber may optionally contain filter material similar to filter material 190a-d. The sampling chamber may also optionally contain an indicator material similar to indicator material 180. The valve assemblies 250, 260 may be similar to valve assemblies 150, 160. Optional o-rings 275a-d may be positioned on each valve assembly 250, 260 prior to coupling the valve assemblies 250, 260 with the corresponding first end 230 and second end 240 of the body 210 via a swaging process.

Figure 3:
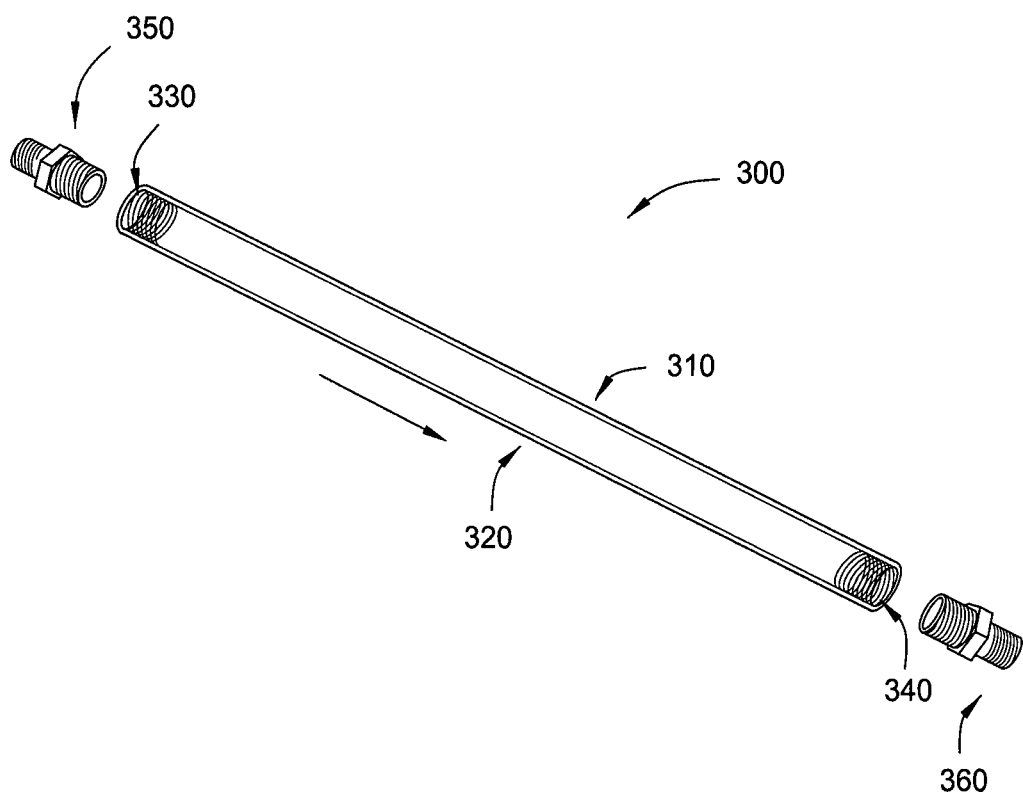
FIG. 3 is a perspective view of another embodiment of a sampling container assembly according to embodiments described herein.

FIG. 3 is a perspective schematic view of another embodiment of a sampling container assembly 300 according to embodiments described herein. The sampling container assembly 300 is similar to the sampling container assembly 100 depicted in FIG. 1 except that the first valve assembly 350 and the second valve assembly 360 are coupled with the body 310 using pipe threads. The sampling container assembly 300 comprises a body 310 similar to body 110 having a first end 330 and a second end 340. The body 310 defines a sampling chamber 320 for holding a fluid. The sampling chamber contains a reactant material (not shown) similar to reactant material 170 and may optionally contain an indicator material similar to indicator material 180 and/or filter material similar to filter material 190. The first end 330 and the second end 340 comprise internal threads and the corresponding first valve assembly 350 and second valve assembly each comprise external threads for mating with the corresponding internal threads. The valve assemblies 350, 360 may be similar to valve assemblies 150, 160.

Figure 4:
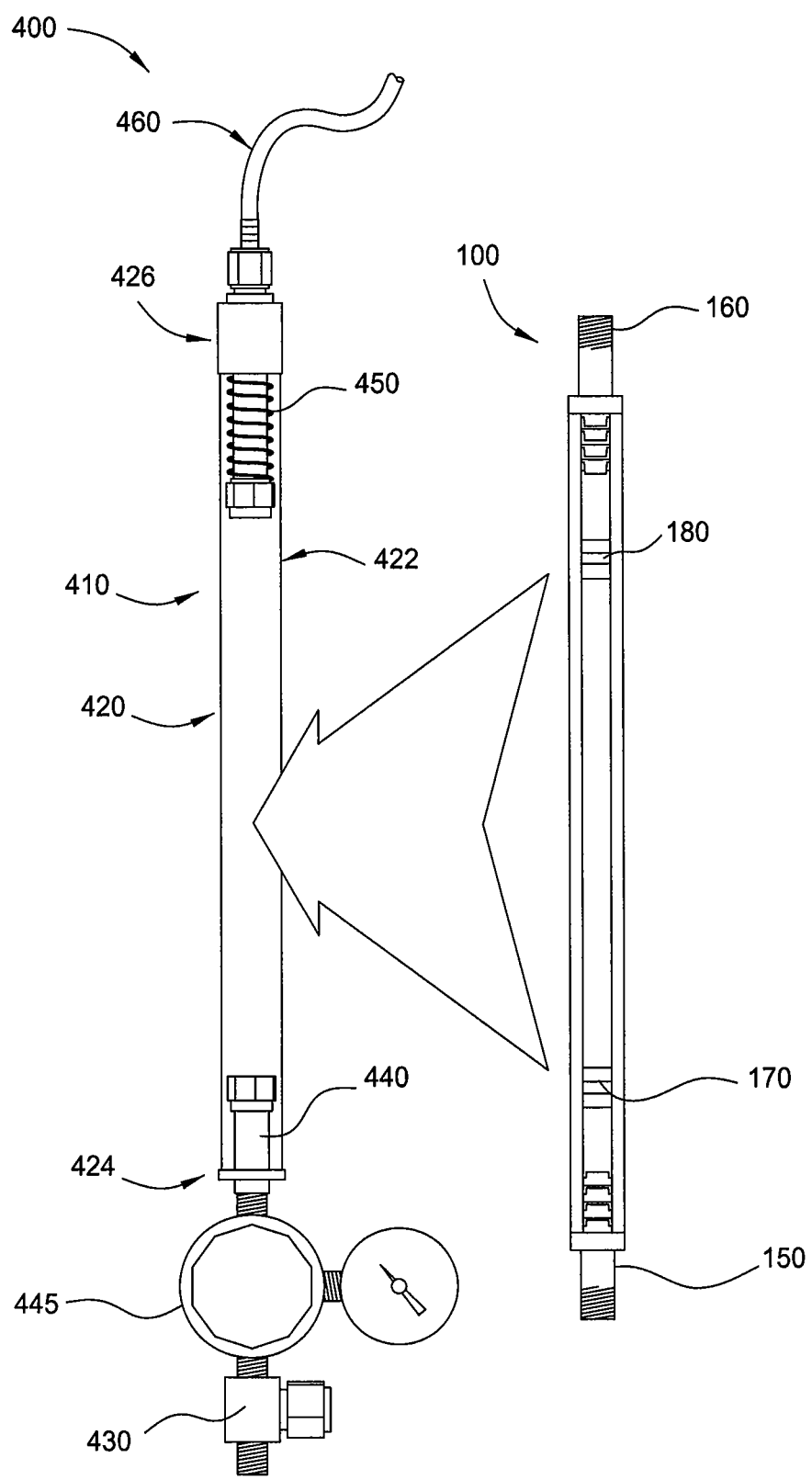
FIG. 4 is a schematic view of one embodiment of a sampling container assembly and a sampling assembly according to embodiments described herein.

FIG. 4 is a schematic view of one embodiment of a sampling container assembly 100 and a sampling assembly 400 according to embodiments described herein. The sampling assembly 400 comprises a sampling device 410 for coupling with a fluid source and sampling container assembly 100 as previously described herein. Although shown as being used together, it should be understood that the sampling device 410 may be used with other sampling containers and the sampling container assembly 100 may be used with other sampling devices.

The sampling device 410 is designed for collecting samples from high pressure sources. The sampling device 410 includes a frame 420 composed of a rigid material, for example, metal, and has a longitudinal body segment 422. A first panel 424 extends from a first end of the body segment 422 and is oriented at a right angle relative to the body segment 422. A second panel 426 extends from a second end of the body segment 422 and is oriented at a right angle relative to the body segment 422. The first panel 424 has an aperture (not visible). The second panel 426 has a corresponding aperture (not visible). Mounted to the first panel 424 and within the aperture of the first panel 424 is a fixed chuck 440. Mounted to the second panel 426 and within the aperture of the second panel 426 is a spring-loaded chuck 450. The spring-loaded chuck 450 and the fixed chuck 440 provide the mounting mechanisms for the sampling container assembly 100.

The sampling device 410 further includes an optional source filter 430 for coupling with the fluid source (not shown) and removing contaminants from the fluid prior to entry of the fluid into the sampling container assembly 100. A pressure regulator 445 is coupled with the fixed chuck 440 for adjusting the pressure of the fluid coming from the fluid source prior to entering the sampling container assembly 100, and a vent hose 460 is coupled with the spring-loaded chuck 450 for venting excess fluid from the sampling container assembly 100.

In operation, the sampling device 410 is coupled with the fluid source, which is typically a high pressure source, via the pressure regulator 445. The pressure regulator 445 reduces the fluid pressure prior to entry of the fluid into the sampling container assembly 100. In certain embodiments, the pressure regulator may reduce the pressure of the fluid from about 3,000 psi down to about 40 psi. The fixed chuck 440 mates with the first valve assembly 150. The fixed chuck 440 comprises a soft gasket and pin that depresses the core in the first valve assembly 150 of the sampling container assembly 100, thereby opening the first valve assembly 150. Without the sampling container assembly 100, the fixed chuck 440 remains sealed with no fluid flowing through the fixed chuck 440. Once the sampling container assembly 100 is inserted, the fixed chuck 440 and the first valve assembly 150 are simultaneously opened allowing fluid to flow into the sampling container assembly 100. The spring-loaded chuck 450 functions similarly to the fixed chuck 440. Typically, the second valve assembly 160 of the sampling container assembly 100 is positioned in the spring-loaded chuck 450 first by compressing the spring of the spring-loaded chuck 450 which simultaneously opens the spring-loaded chuck 450 and the second valve assembly 160. While the spring is compressed, the first valve assembly 150 of the sampling container assembly 100 is aligned with the fixed chuck 440. The spring of the spring-loaded chuck 450 is released thus inserting the first valve assembly 150 into the fixed chuck 440 allowing the flow of fluid into the sampling container assembly 100. The sampling container assembly 100 is positioned within the sampling device 410 with the reactant material 170 positioned closest to the fixed chuck 440 and the indicator material 180 positioned closest to the spring-loaded chuck 450. Fluid flows through the sampling container assembly 100 and reacts with the reactant material 170 until the indicator material 180 indicates, typically via a color change, that the desired amount of the component to be analyzed has been collected. The sampling container assembly 100 is removed from the sampling device 410 and may be shipped to the proper facility for isotopic analysis.

EXAMPLES

Objects and advantages of the embodiments described herein are further illustrated by the following hypothetical example. The particular materials and amounts thereof, as well as other conditions and details, recited in these examples should not be used to limit the embodiments described herein.

A gas containing hydrogen sulfide ($H_2S$) is used as the exemplary fluid with sulfur as the desired component to be collected for isotopic analysis. $H_2S$ is very toxic and dangerous even at low levels. Since $H_2S$ is typically present in varying concentrations, varying concentrations of the gas containing the $H_2S$ will be required to collect the desired amount of sulfur for analysis. For gases containing low concentrations of $H_2S$, it will take more gas and thus a longer flow time to collect the sulfur needed for analysis. Gases containing high concentrations of $H_2S$ will saturate the reactant immediately so the flow time will be short requiring a very low volume of gas. The amount of reactant is based on how much sulfur is needed for analysis. For example, for a gas containing a concentration of about 5 ppm of $H_2S$, about 500 liters of gas is required in order to collect the desired amount of sulfur. For gases containing a concentration of about 50 ppm of $H_2S$, about 50 liters of gas is required in order to collect the desired amount of sulfur. Since the concentration of $H_2S$ is variable and the sampling container assembly 100 is a flow through container the amount of sulfur collected is not limited by the size of the sampling container assembly 100. The sampling container assembly allows for the collection of sample regardless of concentration such that the only variable is time which in essence is volume.

In one example, the reactant material may be zinc carbonate hydroxide ($Zn_5(CO_3)_2(OH)_6$). In the reaction, the hydrogen sulfide in fluid form is converted to ($Zn_5(CO_3)_2 SH(OH)_5$), which is a solid phase compound.

The embodiments described herein provide several advantages over prior methods of collecting hazardous fluid samples. In certain embodiments, after collection in the sampling container assembly, hazardous components are converted to non-hazardous components that can be transported without additional hazardous material restraints. In certain embodiments, the sampling container assembly is compact, lightweight, easy and inexpensive to ship. In certain embodiments, the samples in the sample container assembly do not require further treatment prior to analysis. In certain embodiments, the reactant materials are granular solids rather than liquid solutions, and therefore easier to handle both in the field and in the laboratory.

Further, the results of isotope analysis performed on samples collected using the container assembly and techniques described herein demonstrated that the embodiments described herein are comparable to traditional techniques which utilize reactant solutions. The flow through design of the embodiments described herein allow for the collection of gases such as $H_2S$ at low concentrations by flowing the gas over the reactant materials for longer periods of time. Traditional collection containers typically do not provide sufficient volumes or concentrations of gas to obtain an isotope analysis of a particular component which is problematic since isotope concentrations are largely concentration dependent. The versatile design of the embodiments described herein allow for the contents of the sampling container assembly to be easily modified for the collection and subsequent analysis of other gaseous components of interest.

In another embodiment, a method for sampling a hydrogen sulfide gas includes flowing a gas containing hydrogen sulfide into a sampling container assembly, wherein the container assembly includes a reactant material; reacting the hydrogen sulfide with the reactant material; and converting the hydrogen sulfide to an inert form. In yet another embodiment, the method also includes reacting the hydrogen sulfide with an indicator material for identifying the presence of the hydrogen sulfide.

In another embodiment, a container assembly for sampling a fluid is provided. The sampling container assembly comprises a body defining a sampling chamber having a first end and a second end, a first valve assembly coupled with the first end, a second valve assembly coupled with the second end, an indicator material positioned within the chamber for identifying the presence of a fluid, a reactant material positioned within the sampling chamber for reacting with the fluid, and a filtering material positioned within the sampling chamber for controlling flow of the fluid through the sampling chamber. In certain embodiments, the indicator material is placed downstream relative to the reactant material. In certain embodiments, the indicator material identifies the presence of hydrogen sulfide ($H_2S$) and indicates when the reaction of $H_2S$ with the reactant material is complete. In certain embodiments, the indicator material is selected from the group consisting of: lead acetate, copper sulfate, and combinations thereof. In certain embodiments, the reactant material and the indicator material are each granular solids. In certain embodiments, the body is constructed of metal, plastic, polymer or carbon fiber capable of containing fluid under pressure. In certain embodiments, the body is constructed of a material which is inert with respect to the fluid, reactant material and the indicator material. In certain embodiments at least one of the first valve assembly and the second valve assembly is a self-closing valve assembly. In certain embodiments, the reactant material traps the fluid in an inert (non-hazardous) form. In certain embodiments, the reactant material is selected from the group consisting of: zinc carbonate hydroxide ($Zn_5(CO_3)_2(OH)_6$), iron III oxide hydrate ($2FeO(OH)$), zinc acetate ($2(C_2H_3O_2)_2Zn$), iron oxide ($Fe_2O3$), and combinations thereof. In certain embodiments, the filtering material is selected from the group consisting of: polyethylene (PE) and polytetrafluoroethylene (PTFE) based materials.

While the foregoing is directed to embodiments of the present invention, other and further embodiments of the invention may be devised without departing from the basic scope thereof, and the scope thereof is determined by the claims that follow.

The invention claimed is:

1. A container assembly for sampling a fluid, comprising:
  a body defining a sampling chamber having a first end and a second end;
  a first valve assembly coupled with the first end;
  a reactant material positioned within the sampling chamber for reacting with the fluid; and
  an indicator material for identifying the presence of the fluid, and positioned downstream relative to the reactant material in the sampling chamber.

2. The container assembly of claim 1, further comprising:
  a second valve assembly coupled with the second end, wherein the fluid enters the sampling chamber through the first valve assembly and exits through the second valve assembly.

3. The container assembly of claim 2, wherein the first valve assembly and the second valve assembly are self sealing for retaining the fluid within the chamber.

4. The container assembly of claim 1, further comprising:
  a filtering material positioned within the sampling chamber for controlling flow and separating the indicator material from the reactant material.

5. The container assembly of claim 1, wherein the fluid contains hydrogen sulfide ($H_2S$) and the reactant material converts hydrogen sulfide ($H_2S$) to an inert form.

6. The container assembly of claim 5, wherein the indicator material identifies the presence of $H_2S$ and indicates when the reaction of $H_2S$ with the reactant material is complete.

7. The container assembly of claim 1, wherein the fluid is a gas selected from the group consisting of: hydrogen sulfide ($H_2S$) containing gases, carbon monoxide (CO) containing gases, carbon dioxide ($CO_2$) containing gases, and hydrocarbon containing gases.

8. The container assembly of claim 1, wherein the reactant material is configured to at least partially convert the fluid to an inert form containing a component for analysis.

9. A container assembly for sampling a fluid, comprising:
  a body defining a sampling chamber having a first end and a second end;
  a first valve assembly coupled with the first end;
  a second valve assembly coupled with the second end;
  an indicator material positioned within the sampling chamber for identifying the presence of a fluid;
  a reactant material positioned within the sampling chamber for reacting with the fluid; and
  a filtering material positioned within the sampling chamber for controlling flow of the fluid through the sampling chamber, wherein the indicator material is positioned downstream relative to the reactant material.

10. The container assembly of claim 9, wherein the indicator material identifies the presence of hydrogen sulfide ($H_2S$) and indicates when the reaction of $H_2S$ with the reactant material is complete.

11. The container assembly of claim 10, wherein the indicator material is selected from the group consisting of: lead acetate, copper sulfate, and combinations thereof.

12. The container assembly of claim 10, wherein the reactant material is selected from the group consisting of: zinc carbonate hydroxide ($Zn_5(CO_3)_2(OH)_6$), iron III oxide hydrate ($2FeO(OH)$), zinc acetate ($2(C_2H_3O_2)_2Zn$), iron oxide ($Fe_2O3$), and combinations thereof.

13. The container assembly of claim 9, wherein the reactant material and the indicator material are each granular solids.

14. The container assembly of claim 9, wherein the body is constructed of metal, plastic, polymer or carbon fiber capable of containing fluid under pressure.

15. The container assembly of claim 9, wherein the body is constructed of a material which is inert with respect to the fluid, reactant material and the indicator material.

16. The container assembly of claim 9, wherein at least one of the first valve assembly and the second valve assembly is a self-closing valve assembly.

17. The container assembly of claim 9, wherein the reactant material traps the fluid in an inert (non-hazardous) form.

18. The container of claim 9, wherein the filtering material is selected from the group consisting of: polyethylene (PE) and polytetrafluoroethylene (PTFE) based materials.

19. The container assembly of claim 9, wherein the fluid is a gas selected from the group consisting of: hydrogen sulfide ($H_2S$) containing gases, carbon monoxide (CO) containing gases, carbon dioxide ($CO_2$) containing gases, and hydrocarbon containing gases.

20. The container assembly of claim 9, wherein the reactant material is configured to at least partially convert the fluid to an inert form containing a component for analysis.

21. A container assembly for sampling a fluid, comprising:
  a body defining a sampling chamber having a first end and a second end;
  a first valve assembly coupled with the first end;

a second valve assembly coupled with the second end;

an indicator material positioned within the chamber for identifying the presence of a fluid;

a reactant material positioned within the sampling chamber for reacting with the fluid; and a filtering material positioned within the sampling chamber for controlling flow of the fluid through the sampling chamber, wherein the indicator material identifies the presence of hydrogen sulfide ($H_2S$) and indicates when the reaction of $H_2S$ with the reactant material is complete.

22. The container assembly of claim 21, wherein the body is constructed of metal, plastic, polymer or carbon fiber capable of containing fluid under pressure.

23. The container assembly of claim 21, wherein the body is constructed of a material which is inert with respect to the fluid, reactant material and the indicator material.

24. The container assembly of claim 21, wherein at least one of the first valve assembly and the second valve assembly is a self-closing valve assembly.

25. The container assembly of claim 21, wherein the reactant material traps the fluid in an inert (non-hazardous) form.

26. The container assembly of claim 21, wherein the filtering material is selected from the group consisting of: polyethylene (PE) and polytetrafluoroethylene (PTFE) based materials.

27. The container assembly of claim 21, wherein the reactant material and the indicator material are each granular solids.

* * * * *